(12) United States Patent
Klotzer

(10) Patent No.: US 9,229,931 B2
(45) Date of Patent: Jan. 5, 2016

(54) SYSTEMS AND METHODS FOR MEDICAL IMAGE VIEWER COMPATIBILITY DETERMINATION

(71) Applicant: General Electric Company, Schenectady, NY (US)

(72) Inventor: Jason Dieter Klotzer, Woodside, NY (US)

(73) Assignee: General Electric Company, Schenectady, NY (US)

( * ) Notice: Subject to any disclaimer, the term of this patent is extended or adjusted under 35 U.S.C. 154(b) by 530 days.

(21) Appl. No.: 13/683,438

(22) Filed: Nov. 21, 2012

(65) Prior Publication Data

US 2014/0143651 A1    May 22, 2014

(51) Int. Cl.
G06F 17/22       (2006.01)
G06F 17/30       (2006.01)
G06F 9/54        (2006.01)
G06F 19/00       (2011.01)

(52) U.S. Cl.
CPC *G06F 17/30* (2013.01); *G06F 9/54* (2013.01); *G06F 19/321* (2013.01)

(58) Field of Classification Search
CPC ......... G06F 17/30; G06F 19/321; G06F 9/54; G06F 2209/541
See application file for complete search history.

(56) References Cited

U.S. PATENT DOCUMENTS

| | | | |
|---|---|---|---|
| 6,260,021 B1 * | 7/2001 | Wong | G06F 19/321 705/1.1 |
| 7,106,479 B2 * | 9/2006 | Roy et al. | 358/3.27 |
| 7,386,462 B2 * | 6/2008 | Silva-Craig et al. | 705/2 |
| 8,195,481 B2 * | 6/2012 | Backhaus | 705/2 |
| 8,520,978 B2 * | 8/2013 | Jakobovits | 382/299 |
| 8,626,527 B1 * | 1/2014 | Reicher et al. | 705/2 |

(Continued)

FOREIGN PATENT DOCUMENTS

EP    1217556 A2    6/2002

OTHER PUBLICATIONS

Valente et al., "A RESTful Image Gateway for Multiple Medical Image Repositories", 2012 IEEE, pp. 356-364.*

(Continued)

*Primary Examiner* — Maikhanh Nguyen
(74) *Attorney, Agent, or Firm* — Hanley, Flight and Zimmerman, LLC

(57) ABSTRACT

Certain examples provide systems and methods to determine client compatibility. An example method includes receiving a request at an image viewer from a client browser for display of medical image data. The example method includes providing a temporary view to the client browser in response to the request. The example method includes determining client compatibility with the viewer and an associated server in the background at a client device executing the client browser while the temporary view is displayed at the client browser. The example method includes requesting the image data from the server based on the client compatibility determination. The example method includes rendering the image data and providing to the client browser based on the client compatibility determination, the rendering and presentation of the image data modified to enable or disable capability of at least one of the viewer and the server based on the client compatibility determination.

14 Claims, 3 Drawing Sheets

(56) References Cited

U.S. PATENT DOCUMENTS

| | | | |
|---|---|---|---|
| 2002/0016718 A1* | 2/2002 | Rothschild et al. | 705/2 |
| 2002/0091659 A1* | 7/2002 | Beaulieu | G06F 19/321 706/62 |
| 2002/0133373 A1* | 9/2002 | Silva-Craig et al. | 705/2 |
| 2006/0242148 A1* | 10/2006 | Rothpearl | G06F 17/30265 1/1 |
| 2006/0293921 A1* | 12/2006 | McCarthy et al. | 705/2 |
| 2008/0263048 A1* | 10/2008 | Wise | 707/9 |
| 2009/0132285 A1* | 5/2009 | Jakobovits | 705/3 |
| 2009/0274384 A1* | 11/2009 | Jakobovits | 382/254 |
| 2010/0082369 A1* | 4/2010 | Prenelus et al. | 705/3 |
| 2010/0202510 A1* | 8/2010 | Kyle | 375/240.01 |
| 2011/0015941 A1* | 1/2011 | Backhaus | 705/2 |
| 2011/0110568 A1* | 5/2011 | Vesper | G06F 19/321 382/128 |
| 2012/0084350 A1* | 4/2012 | Xie | 709/203 |
| 2012/0191793 A1* | 7/2012 | Jakobovits | G06F 19/321 709/206 |

OTHER PUBLICATIONS

Kulkarni et al. "NetraRIS—a Web based DICOM Viewer", 2012 International Journal of Computer Applications, pp. 40-44.*

D. Kohn, "Imaging world shows DICOM standard works", Mar. 1995, Health Management Technology, pp. 20-24.*

Leadtools, "HTML5 Zero Footprint Viewer for Dicom and Pacs-CodeProject", retrieved from the Internet on Jun. 18, 2012, 6 pages.

Jacinto, Hector et al, "A Web Interface for 3D Visualization and Interactive Segmentation of Medical Images", Aug. 4, 2012, pp. 51-58.

Anonymous, "The Graceful WebSocket", Google Project Hosting, retrieved from the internet on Apr. 14, 2012, 1 page.

Leadtools, "Using the HTML5 Medical Web Viewer", retrieved from the Internet on Jul. 12, 2012, 1 page.

European Paten Office, "Search Report and Written Opinion", issued in connection with European Patent application No. 131936841, mailed on Mar. 7, 2014, 10 pages.

* cited by examiner

SYSTEMS AND METHODS FOR MEDICAL IMAGE VIEWER COMPATIBILITY DETERMINATION

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

BACKGROUND

Prior to the rapid onset of digital imaging, patient images were "printed" to film. The film was "hung" and viewed by radiologists, who would then dictate a report. Reports were transcribed by individuals ranging for administrative staff to medical transcriptionists and sent to ordering physician via mail or fax. Critical results were delivered by phone or pager and business statistics were managed via paper reports and spreadsheets.

As information systems for radiology came to market, the first commercially available solutions addressed the needs of the radiologist and the radiology department. These included Radiology Information Systems (RIS) and dictation transcription systems. RIS systems managed the ordering, scheduling, patient and management reporting processes while radiologists were still reading from film.

As modalities started to support the digital display of images on workstations connected to the acquisition device, Picture Archiving and Communications Systems (PACS) came to market. These centrally store images and provide radiologists with the tools to read studies on networked computer monitors, replacing both film and modality workstations.

Over time, the needs of the market have evolved from supporting specialized radiologist workflows to supporting the open and dynamic needs of the enterprise and the community. The vendor community has added systems to manage the need for advanced technologies for better diagnosis; the sharing of images between providers and organizations; to support collaboration between radiologists, physicians and teams providing care for the patient; to close the loop on reporting of critical results and manage the growing storage requirements. Often these are disparate, best-of breed systems that may or may not interoperate, increasing cost and decreasing productivity.

BRIEF SUMMARY

Certain examples provide systems and methods for client compatibility detection.

Certain examples provide a system including a medical image viewer facilitating rendering and display of medical image data to a client browser from a server. The example viewer is configured to receive a request from the client browser for display of medical image data. The example viewer is configured to provide a temporary view to the client browser in response to the request. The example viewer is configured to determine client compatibility with the viewer and server in the background while the temporary view is displayed at the client browser. The example viewer is configured to request the medical image data from the server based on the client compatibility determination. The example viewer is configured to render the medical image data and providing to the client browser based on the client compatibility determination, the rendering and presentation of the medical image data modified to enable or disable capability of at least one of the viewer and the server based on the client compatibility determination.

Certain examples provide a tangible computer-readable storage medium including computer program code to be executed by a processor, the computer program code, when executed, to implement a method. The example method includes receiving a request at an image viewer from a client browser for display of medical image data. The example method includes providing a temporary view to the client browser in response to the request. The example method includes determining client compatibility with the viewer and an associated server in the background at a client device executing the client browser while the temporary view is displayed at the client browser. The example method includes requesting the medical image data from the server based on the client compatibility determination. The example method includes rendering the medical image data and providing to the client browser based on the client compatibility determination, the rendering and presentation of the medical image data modified to enable or disable capability of at least one of the viewer and the server based on the client compatibility determination.

Certain examples facilitate a method including receiving a request at an image viewer from a client browser for display of medical image data. The example method includes providing a temporary view to the client browser in response to the request. The example method includes determining client compatibility with the viewer and an associated server in the background at a client device executing the client browser while the temporary view is displayed at the client browser. The example method includes requesting the medical image data from the server based on the client compatibility determination. The example method includes rendering the medical image data and providing to the client browser based on the client compatibility determination, the rendering and presentation of the medical image data modified to enable or disable capability of at least one of the viewer and the server based on the client compatibility determination.

Figure 1:
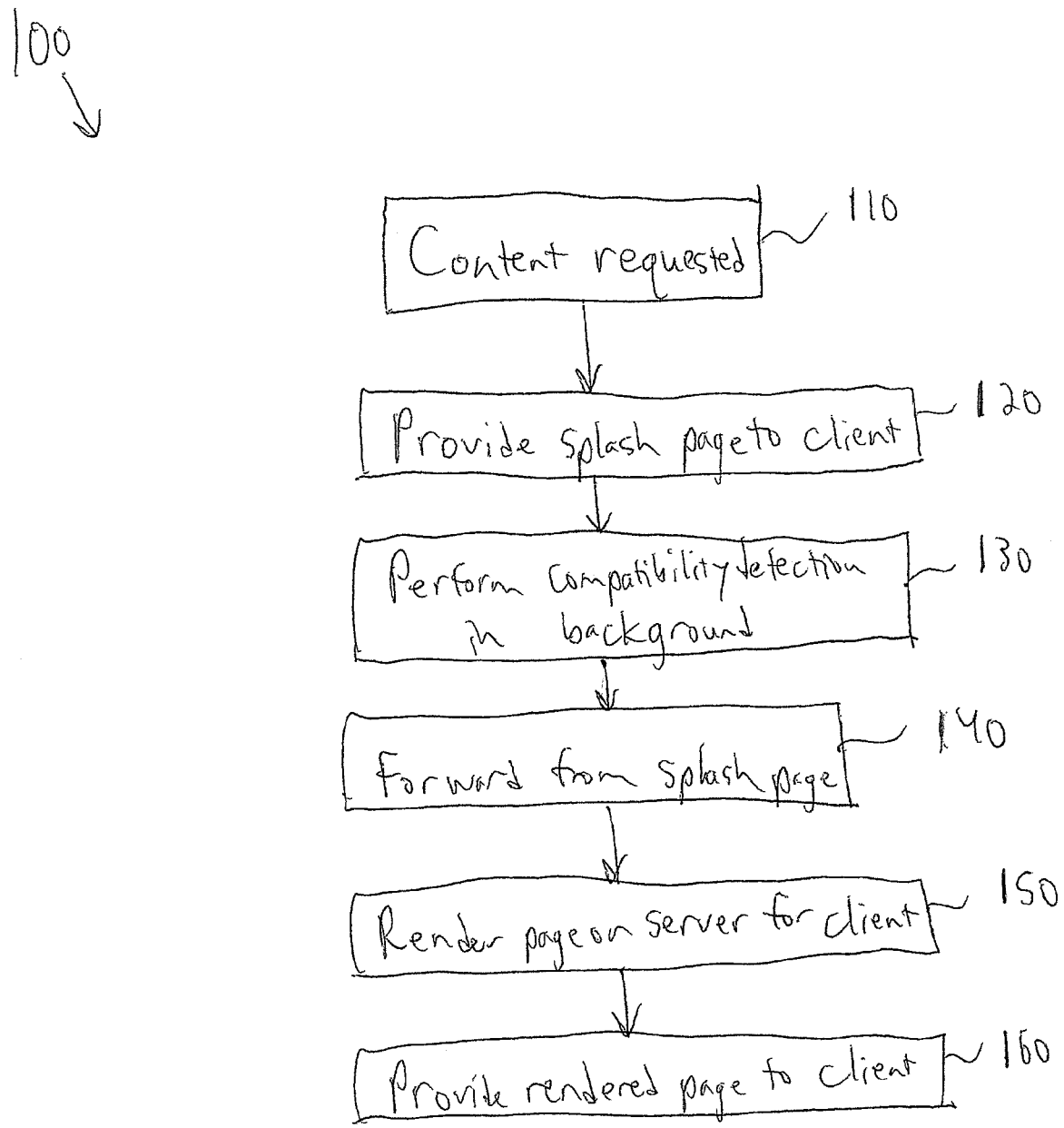
FIG. 1 illustrates a flow diagram of an example method to facilitate compatibility detection.

The foregoing summary, as well as the following detailed description of certain examples of the present invention, will be better understood when read in conjunction with the appended drawings. For the purpose of illustrating the invention, certain examples are shown in the drawings. It should be understood, however, that the present invention is not limited to the arrangements and instrumentality shown in the attached drawings.

DETAILED DESCRIPTION OF CERTAIN EMBODIMENTS

I. Overview

In certain examples, a unified viewer workspace for radiologists and clinicians brings together capabilities with innovative differentiators that drive optimal performance through connected, intelligent workflows. The unified viewer workspace enables radiologist performance and efficiency, improved communication between the radiologist and other clinicians, and image sharing between and across organizations, reducing cost and improving care.

The unified imaging viewer displays medical images, including mammograms and other x-ray, computed tomography (CT), magnetic resonance (MR), ultrasound, and/or other images, and non-image data from various sources in a common workspace. Additionally, the viewer can be used to create, update annotations, process and create imaging models, communicate, within a system and/or across computer networks at distributed locations.

In certain examples, the unified viewer implements smart hanging protocols, intelligent fetching of patient data from within and outside a picture archiving and communication system (PACS) and/or other vendor neutral archive (VNA). In certain examples, the unified viewer supports image exchange functions and implements high performing streaming, as well as an ability to read across disparate PACS without importing data. The unified viewer serves as a "multiology" viewer, for example.

In certain examples, a native reading worklist is provided via the unified viewer. The worklist is intuitive and user defined and can include multi-identifier, multi-document, and multi-institution, for example.

Certain examples provide workflow integration via the unified viewer. Workflow integration includes integration with reporting systems, worklists, voice recognition (VR), electronic medical records (EMR); exporting of measurements; exporting of exam notes; thin slice management; etc.

Many websites provide compatibility detection code in one of the two locations—client-side or server-side. For client-side compatibility detection, a tool (such as 'modernizer.js') detects client compatibility, enables one or more flags, and executes code based on the enabled flags. A problem with this approach is that there is a lot of "dead code" in the client device that will not be executed because it is not relevant for the currently executing client application. On the server-side, compatibility is determined by the server making a "best guess" regarding a type of client that is connected to the server, based on one or more hypertext transfer protocol (HTTP) variables that are passed from client to server. Variables include browser version, basic client hardware information, etc. However, this server-side approach to compatibility detection is far from accurate in many cases because the server has to maintain a map of the features that are supported in the client and only return code relevant for those features.

Incorrect compatibility detection can result in loss of functionality and/or unexpected results. Compatibility detection not only determines if something is not compatible, but also provides a fallback technology so that under no circumstances does the product not function, for example. For example, detection of a presence of/support for WebGL functionality can be a part of compatibility detection. WebGL functions may not be available to a JavaScript Engine. By detecting if WebGL is available in the browser, the browser can exercise the WebGL functionality, or if not available, then the viewer can implement the same functionality using a different but similar feature such as Canvas rendering, etc.

As another example, compatibility detection determines whether a system supports WebSockets for data communication. If so, then WebSockets are used to transfer, for example, requested image data to from storage to a viewer. If WebSockets are not available or supported, then a Web Service, for example, can be used to transfer the image data.

Certain examples provide a zero footprint approach to "intelligent" compatibility detection. FIG. 1 illustrates a flow diagram of an example method 100 to facilitate compatibility detection for a ZFP viewer. At block 110, a client requests a page or screen of content. For example, a web client (e.g., a web browser) requests a page of content based on user input, and the request is communicated via a zero footprint (ZFP) viewer. At block 120, the client is provided with a splash page (e.g., a graphic, preview image, product logo, status text (e.g., "Loading viewer . . . "), hourglass, etc.), which is an introductory page to provide the client with a status notification or initial information while background detection code (e.g., 'modernizer.js', etc.) is executed (e.g., by a compatibility detector associated with a ZFP viewer) to accurately detect client compatibility.

At block 130, the compatibility detection is performed in the background while the splash screen is displayed. For example, the compatibility detection analyses the elements that are part of a current JavaScript document object model (DOM) to determine features available to the client. For example, compatibility detection tries to create various types that are specific to support of features in the browser. An example is creating a WebSocket instance by checking if the "WebSocket" type exists in the DOM, trying to invoke typed array features for typed array support in the browser, etc.

At block 140, the client is forwarded from the splash page to the page or content screen that was originally requested by the client. In certain examples, since the requested page is a server-side rendered page, the values that were originally detected on the client are passed to the server. A result of the compatibility detection (e.g., a version of the client web browser, client browser support for certain webpage functionality, etc.) factors into the information passed to the server and the rendered of the page by the server, for example.

At block 150, based on the input values passed to the server from the client, the server accurately renders the client page to be displayed at the client. At block 160, the server-side rendered page of content is provided to the client for display (e.g., via a ZFP viewer and web client).

Thus, certain examples provide a more efficiently rendered webpage of content (e.g., reduced or eliminated "dead code") and a more accurate compatibility, since the compatibility information comes from the client.

Figure 2:
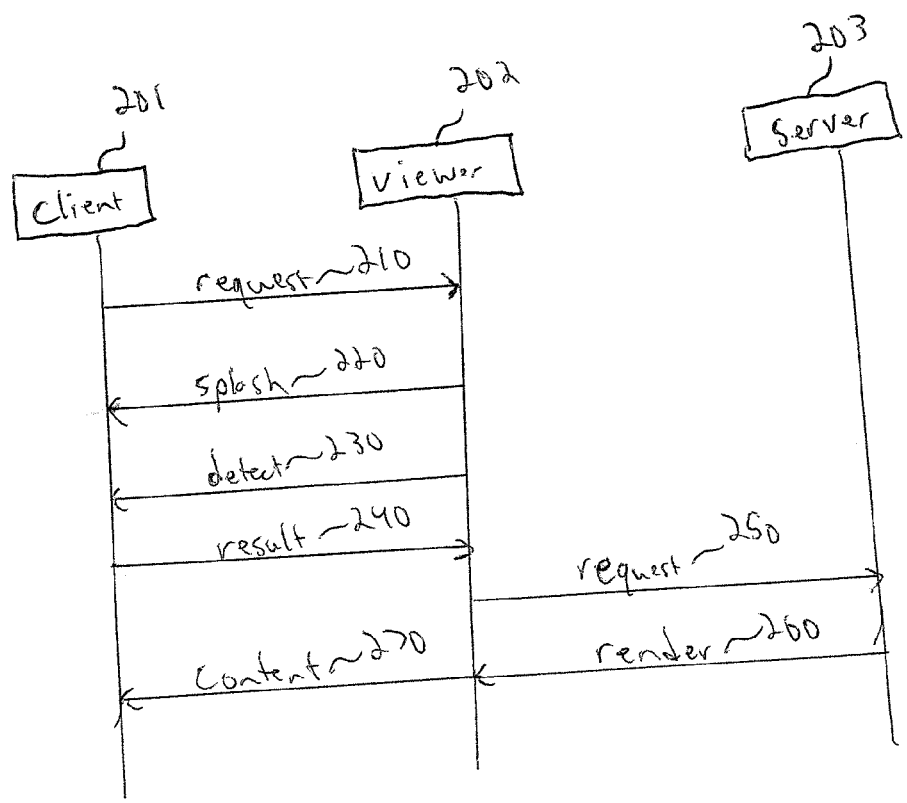
FIG. 2 illustrates an example system and associated data flow to determine client compatibility with server capability.

FIG. 2 illustrates an example system and associated data flow 200 to determine client compatibility with server capability. The example system includes a client browser 201, a viewer 202, and a server 203.

At 210, the client browser 201 sends a request for content to the viewer 202 (e.g., a zero footprint (ZFP) viewer). For example, the client browser 201 requests an HTML5-based image study review to be generated via the viewer 202 for display and manipulation on the client browser 201 on a client device.

At 220, a "splash" screen (e.g., a temporary, placeholder, or introductory view) is provided to the client 201 from the viewer 202. For example, a lower-resolution introductory image, an "about" screen, a welcome page, etc., is shown to a user at the client device 201 while compatibility determination proceeds in the background.

At 230, the viewer 202 determines a compatibility between functionality of the viewer 202 and the client browser 201. For example, the viewer 202 queries configuration information from the client browser 201 and/or associated client device (e.g., WebGL support, WebSocket support, operating system version, browser version, etc.).

At 240, a result is provided to the viewer 202. Based on the compatibility detection result, some or all functionality of the viewer 202 and/or server 203 can be provided in content to the client 201. For example, if supported, WebSockets can be used to transfer image data from data storage to the client 201 (e.g., via a server and/or other streaming engine). If graphics capabilities, such as WebGL, are supported, then those capabilities are utilized in rendering and displaying images at the client 201, for example. If not supported, one or more fallback (e.g., lesser) capabilities are provided to display some or all of the requested information, for example. Thus, at 250, the viewer 201 sends a request for content to the server 203 based on the outcome of the compatibility detection. At 260, requested content (e.g., image data, etc.) is rendered at the server 203. At 270, the rendered content is provided to the client 201 for display.

In certain examples, compatibility detection can be used to help provide a zero footprint platform and viewer that facilitates display, manipulation, reformatting, etc., of medical images (e.g., DICOM medical images) without a requirement for client installation, download of viewer component(s) at the client, etc., and which can run on virtually any hardware that is able to support an appropriate browser (e.g., an HTML5 browser). Certain examples provide a viewer component to facilitate image rendering and manipulation; a middle-tier server to support transcoding of data (e.g., DICOM data) for image pixels, metadata, and non-image objects. Using this novel architecture, efficient web based browsing of DICOM image studies can be accomplished without the addition of any extra components at the client system, for example.

Figure 3:
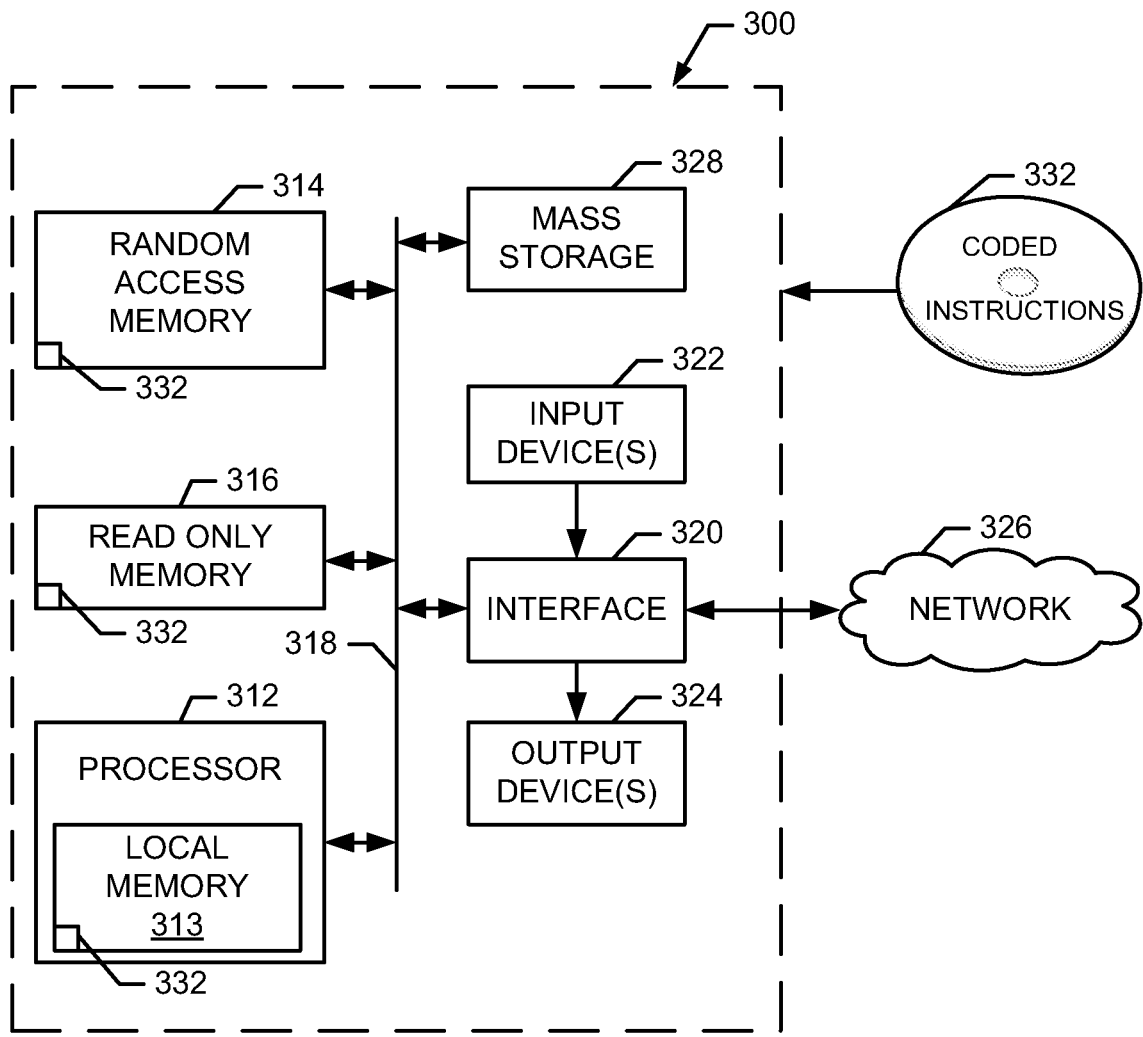
FIG. 3 is a block diagram of an example processor system that may be used to implement systems and methods described herein.

FIG. 3 is a block diagram of an example processor system 310 that may be used to implement systems and methods described herein. As shown in FIG. 3, the processor system 310 includes a processor 312 that is coupled to an interconnection bus 314. The processor 312 may be any suitable processor, processing unit, or microprocessor, for example. Although not shown in FIG. 3, the system 310 may be a multi-processor system and, thus, may include one or more additional processors that are identical or similar to the processor 312 and that are communicatively coupled to the interconnection bus 314.

The processor 312 of FIG. 3 is coupled to a chipset 318, which includes a memory controller 320 and an input/output ("I/O") controller 322. As is well known, a chipset typically provides I/O and memory management functions as well as a plurality of general purpose and/or special purpose registers, timers, etc. that are accessible or used by one or more processors coupled to the chipset 318. The memory controller 320 performs functions that enable the processor 312 (or processors if there are multiple processors) to access a system memory 324 and a mass storage memory 325.

The system memory 324 may include any desired type of volatile and/or nonvolatile memory such as, for example, static random access memory (SRAM), dynamic random access memory (DRAM), flash memory, read-only memory (ROM), etc. The mass storage memory 325 may include any desired type of mass storage device including hard disk drives, optical drives, tape storage devices, etc.

The I/O controller 322 performs functions that enable the processor 312 to communicate with peripheral input/output ("I/O") devices 326 and 328 and a network interface 330 via an I/O bus 332. The I/O devices 326 and 328 may be any desired type of I/O device such as, for example, a keyboard, a video display or monitor, a mouse, etc. The network interface 330 may be, for example, an Ethernet device, an asynchronous transfer mode ("ATM") device, an 802.11 device, a DSL modem, a cable modem, a cellular modem, etc. that enables the processor system 310 to communicate with another processor system.

While the memory controller 320 and the I/O controller 322 are depicted in FIG. 3 as separate blocks within the chipset 318, the functions performed by these blocks may be integrated within a single semiconductor circuit or may be implemented using two or more separate integrated circuits.

It should be understood by any experienced in the art that the inventive elements, inventive paradigms and inventive methods are represented by certain exemplary embodiments only. However, the actual scope of the invention and its inventive elements extends far beyond selected embodiments and should be considered separately in the context of wide arena of the development, engineering, vending, service and support of the wide variety of information and computerized systems with special accent to sophisticated systems of high load and/or high throughput and/or high performance and/or distributed and/or federated and/or multi-specialty nature.

Certain embodiments contemplate methods, systems and computer program products on any machine-readable media to implement functionality described above. Certain embodiments may be implemented using an existing computer processor, or by a special purpose computer processor incorporated for this or another purpose or by a hardwired and/or firmware system, for example.

One or more of the components of the systems and/or steps of the methods described above may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device. Certain embodiments of the present invention may omit one or more of the method steps and/or perform the steps in a different order than the order listed. For example, some steps may not be performed in certain embodiments of the present invention. As a further example, certain steps may be performed in a different temporal order, including simultaneously, than listed above.

Certain embodiments include computer-readable media for carrying or having computer-executable instructions or data structures stored thereon. Such computer-readable media may be any available media that may be accessed by a general purpose or special purpose computer or other machine with a processor. By way of example, such computer-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of computer-executable instructions or data structures and which can be accessed by a general purpose or special purpose computer or other machine with a processor. Combinations of the above are also included within the scope of computer-readable media. Computer-executable instructions comprise, for example, instructions and data which cause a general purpose computer, special purpose computer, or special purpose processing machines to perform a certain function or group of functions.

Generally, computer-executable instructions include routines, programs, objects, components, data structures, etc., that perform particular tasks or implement particular abstract data types. Computer-executable instructions, associated data structures, and program modules represent examples of program code for executing steps of certain methods and systems disclosed herein. The particular sequence of such executable instructions or associated data structures represent examples of corresponding acts for implementing the functions described in such steps.

Embodiments of the present invention may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, minicomputers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing the overall system or portions of embodiments of the invention might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated computer-readable media provide nonvolatile storage of computer-executable instructions, data structures, program modules and other data for the computer.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A system comprising:
a medical image viewer, including a processor, facilitating rendering and display of medical image data to a client browser from a server, the viewer:
receives a request from the client browser for display of medical image data;
provides a temporary view to the client browser in response to the request;
determines client compatibility with the viewer and server in the background while the temporary view is displayed at the client browser;
requests the medical image data from the server based on the client compatibility determination;
renders the medical image data and providing to the client browser based on the client compatibility determination, the rendering and presentation of the medical image data modified to enable or disable capability of at least one of the viewer and the server based on the client compatibility determination;
where an output page is to be rendered before being passed to the client browser to facilitate zero footprint image display and manipulation at the client browser, the zero footprint image display and manipulation supported by the viewer and the server based on the client compatibility determination;
wherein the output page is to be rendered to reduce dead code in the output that is unused as a result of the client compatibility determination.

2. The system of claim 1, wherein the viewer includes preferred functionality and fallback functionality for the rendering and presentation of the medical image data, one of the preferred functionality and the fallback functionality to be selected by the viewer based on the client compatibility determination.

3. The system of claim 1, wherein the client compatibility determination is to analyze elements in a document object model to determine features available to the client browser.

4. The system of claim 1, wherein the temporary view is to provide introductory or status information via the client browser while the compatibility determination is occurring in the background on a device executing the client browser.

5. The system of claim 1, wherein a JavaScript is used to determine client compatibility at a client device executing the client browser.

6. A tangible, non-transitory, computer-readable storage medium including computer program code to be executed by a processor, the computer program code, when executed, to implement a method comprising:
receiving a request at an image viewer from a client browser for display of medical image data;
providing a temporary view to the client browser in response to the request;
determining client compatibility with the viewer and an associated server in the background at a client device executing the client browser while the temporary view is displayed at the client browser;
requesting the medical image data from the server based on the client compatibility determination;
rendering the medical image data and providing to the client browser based on the client compatibility determination, the rendering and presentation of the medical image data modified to enable or disable capability of at least one of the viewer and the server based on the client compatibility determination
where an output page is rendered before being passed to the client browser to facilitate zero footprint image display and manipulation at the client browser, the zero footprint image display and manipulation supported by the viewer and the server based on the client compatibility determination,
wherein the output page is rendered to reduce dead code in the output that is unused as a result of the client compatibility determination.

7. The computer-readable storage medium of claim 6, wherein the viewer includes preferred functionality and fallback functionality for the rendering and presentation of the medical image data, one of the preferred functionality and the fallback functionality to be selected by the viewer based on the client compatibility determination.

8. The computer-readable storage medium of claim 6, wherein the client compatibility determination analyzes elements in a document object model to determine features available to the client browser.

9. The computer-readable storage medium of claim 6, wherein the temporary view is to provide introductory or status information via the client browser while the compatibility determination is occurring in the background on a device executing the client browser.

10. A method comprising:
receiving a request at an image viewer from a client browser for display of medical image data;
providing a temporary view to the client browser in response to the request;
determining client compatibility with the viewer and an associated server in the background at a client device executing the client browser while the temporary view is displayed at the client browser;
requesting the medical image data from the server based on the client compatibility determination;
rendering the medical image data and providing to the client browser based on the client compatibility determination, the rendering and presentation of the medical image data modified to enable or disable capability of at least one of the viewer and the server based on the client compatibility determination
where an output page is rendered before being passed to the client browser to facilitate zero footprint image display and manipulation at the client browser, the zero footprint image display and manipulation supported by the viewer and the server based on the client compatibility determination
wherein the output page is rendered to reduce dead code in the output that is unused as a result of the client compatibility determination.

11. The method of claim 10, wherein the viewer includes preferred functionality and fallback functionality for the rendering and presentation of the medical image data, one of the preferred functionality and the fallback functionality to be selected by the viewer based on the client compatibility determination.

12. The method of claim 10, wherein the client compatibility determination analyzes elements in a document object model to determine features available to the client browser.

13. The method of claim 10, wherein the temporary view is to provide introductory or status information via the client browser while the compatibility determination is occurring in the background on a device executing the client browser.

14. The method of claim 10, wherein a JavaScript is used to determine client compatibility at a client device executing the client browser.

* * * * *